US012514437B2

(12) United States Patent
Limberg et al.

(10) Patent No.: US 12,514,437 B2
(45) Date of Patent: Jan. 6, 2026

(54) MEDICAL DEVICE EXTENSION

(71) Applicant: Boston Scientific Scimed, Inc., Maple Grove, MN (US)

(72) Inventors: Pauline R. Limberg, Northborough, MA (US); Nathan T. Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 410 days.

(21) Appl. No.: 18/164,991

(22) Filed: Feb. 6, 2023

(65) Prior Publication Data

US 2023/0255456 A1 Aug. 17, 2023

Related U.S. Application Data

(60) Provisional application No. 63/267,843, filed on Feb. 11, 2022.

(51) Int. Cl.
*A61B 1/015* (2006.01)
*A61B 1/00* (2006.01)

(52) U.S. Cl.
CPC .......... *A61B 1/015* (2013.01); *A61B 1/00128* (2013.01)

(58) Field of Classification Search
CPC .. A61B 1/00128; A61B 1/015; A61B 1/00124
USPC .......................................................... 600/132
See application file for complete search history.

(56) References Cited

U.S. PATENT DOCUMENTS

| | | | | |
|---|---|---|---|---|
| 7,582,056 | B2 | 9/2009 | Noguchi et al. | |
| 2006/0106285 | A1* | 5/2006 | Boulais .................. | A61B 1/128 600/156 |
| 2012/0289858 | A1* | 11/2012 | Ouyang ............. | A61B 1/00101 600/562 |
| 2020/0245855 | A1 | 8/2020 | Tamura et al. | |

FOREIGN PATENT DOCUMENTS

WO 2021262646 A1 12/2021

OTHER PUBLICATIONS

International Search Report and Written Opinion in PCT/US2023/062041 (4 pages).

* cited by examiner

*Primary Examiner* — Aaron B Fairchild
(74) *Attorney, Agent, or Firm* — Bookoff McAndrews, PLLC

(57) ABSTRACT

A medical system comprising a scope including a shaft, a handle, and a first tube extending from the handle; medical equipment including a processor and a first fluid source; and a second tube comprising: a first end including a first connector engaging the processor, and a second connector engaging the first fluid source, a second end including a third connector engaging the first tube, a first channel configured to convey data from the processor to the scope, wherein the first channel extends between the first connector and the third connector, and a second channel configured to convey fluid from the first fluid source to the scope, wherein the second channel extends between the second connector and a first fluid outlet of the second tube, wherein the second channel includes a first pump configured to pressurize the fluid passing through the second channel.

20 Claims, 4 Drawing Sheets

MEDICAL DEVICE EXTENSION

CROSS-REFERENCE TO RELATED APPLICATIONS

This application claims the benefit of priority under 35 U.S.C. § 119 from U.S. Provisional Application No. 63/267,843, filed Feb. 11, 2022, which is incorporated by reference herein in its entirety.

TECHNICAL FIELD

This disclosure relates generally to a medical system and aspects thereof. More particularly, at least some embodiments of the disclosure relate to a medical system including an extension or an elongated feature between a medical device, e.g., a scope, and equipment supporting the medical device.

BACKGROUND

During certain medical procedures, e.g., endoscopy, the scope's umbilicus may restrict a range of motion for various reasons, such as length, tangling, etc. This can restrict the ability of an endoscopist to effectively and/or efficiently conduct the procedure. Various devices or equipment may be used to reposition or manipulate the umbilicus in an effort to improve range of motion. Such devices or equipment, however, may not provide sufficient range of motion to the endoscopist.

SUMMARY OF THE DISCLOSURE

According to an example, a medical system may comprise a scope including a shaft, a handle, and a first tube extending from the handle, medical equipment including a processor and a first fluid source, and a second tube comprising: a first end including a first connector engaging the processor, and a second connector engaging the first fluid source, a second end including a third connector engaging the first tube, a first channel configured to convey data from the processor to the scope, wherein the first channel extends between the first connector and the third connector, and a second channel configured to convey fluid from the first fluid source to the scope, wherein the second channel extends between the second connector and a first fluid outlet of the second tube, wherein the second channel includes a first pump configured to pressurize the fluid passing through the second channel, the first pump being closer to either the second end of second tube or the first end of the second tube.

In another example, the first channel may include a booster configured to boost the transmission of data from the processor to the scope, wherein the booster is closer to the second end of the second tube than the first end of the second tube. The first pump may be closer to the second end of the second tube than the first end of the second tube. The first pump may be configured to at least restore a loss of fluid pressure by which the first fluid was initially conveyed from the first fluid source to the second channel. The medical system may further comprise a secondary water source downstream of the first pump, wherein the secondary water source is located at a junction between the first end and the second end of the second tube, wherein the first fluid source is air, and wherein the secondary water source is in fluid communication with the second channel, so that the first pump is configured to pressurize the secondary water source.

In another example, the first pump may be closer to the first end of the second tube than the second end of the second tube. The medical system may further comprise a secondary water source downstream of the first pump, wherein the secondary water source is located at a same location as the medical equipment, wherein the first fluid source is air, and wherein the secondary water source is in fluid communication with the second channel, so that the first pump is configured to pressurize the secondary water source.

In another example, the medical equipment may further include a second fluid source, and the second tube may further comprise a third channel configured to convey fluid from a second fluid source, wherein the third channel is in fluid communication with the second fluid source, and wherein the third channel includes a second pump configured to pressurize the fluid passing through the third channel. The third channel may extend between a first fluid inlet of the second tube and a second fluid outlet of the second tube, and the medical system may further comprise a first tubing extending between the first fluid inlet and the second fluid source, and a second tubing extending between the second fluid outlet and the scope. The medical equipment may further include a suction source, and the second tube may further comprise a fourth channel configured to convey fluid from the suction source, the fourth channel being in fluid communication with the suction source, and the fourth channel including a third pump configured to pressurize the fluid passing through the third channel. The fourth channel may extend between a second fluid inlet of the second tube and a third fluid outlet of the second tube, and the medical system may further comprise a third tubing extending between the second fluid inlet and the suction source, and a fourth tubing extending between the third fluid outlet and the scope. The second fluid source may be water, and the suction source may provide suction. The first pump, the second pump, and the third pump may be closer to the second end of the second tube than the first end of the second tube. The second end of the second tube may include a seal configured to inhibit leakage of fluid from the first fluid source from the second end.

According to an example, a medical system may comprise a scope including a shaft, a handle, and a first tube extending from the handle, medical equipment including a vacuum source, a second tube comprising a first end engaging the medical equipment, a second end engaging the first tube, and a first channel in fluid communication with the vacuum source and the scope, such that the first channel is configured to convey suction from the vacuum source to the scope, wherein the first channel includes a pump configured to pressurize the vacuum passing through the first channel, and a housing coupled to the second tube, wherein the housing includes a cavity configured to trap material drawn proximally via the suction. The first channel may include a first portion a second portion, and a rotatable connector positioned therebetween, wherein the rotatable connector may rotate between a first position and a second position. In the first position of the rotatable connector, a flow of suction may be routed through the second portion of the first channel and into the cavity of the housing, thereby trapping the material in the cavity. In the second position of the rotatable connector, the flow of suction may bypass the cavity of the housing, and may be routed directly from the scope to the medical equipment.

According to another example, a medical device may comprise a tube including a first end configured to engage medical equipment and a second end configured to engage an umbilicus of a scope, the tube including: a first channel configured to convey a first fluid from the medical equipment to a secondary water source, wherein the first channel includes a first pump configured to pressurize the fluid passing through the first pump, a second channel configured to convey a second fluid from the medical equipment to the scope, wherein the second channel includes a second pump configured to pressurize the fluid passing through the second pump, and a third channel configured to convey a third fluid from the medical equipment to the scope, wherein the third channel includes a third pump configured to pressurize the fluid passing through the third pump, wherein all of the first pump, the second pump, and the third pump are closer to the second end of second tube or closer to the first end of the second tube.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the disclosure, examples of which are illustrated in the accompanying drawings. Wherever possible, the same or similar reference numbers will be used through the drawings to refer to the same or like parts. The term “distal” refers to a portion farthest away from a user when introducing a device into a subject (e.g., patient). By contrast, the term “proximal” refers to a portion closest to the user when placing the device into the subject.

Both the foregoing general description and the following detailed description are exemplary and explanatory only and are not restrictive of the features, as claimed. As used herein, the terms “comprises,” “comprising,” “having,” “including,” or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, “about,” “substantially,” “generally,” and “approximately” are used to indicate a possible variation of ±10% in a stated value or characteristic.

Embodiments of the disclosure may solve one or more of the limitations in the art. The scope of the disclosure, however, is defined by the attached claims and not the ability to solve a specific problem.

The disclosure is drawn to medical systems including a medical device, medical equipment supporting the device, and an extension between the device and the equipment. The extension lengthens the connection between the medical device and the equipment, allowing a user to more effectively reposition or manipulate the medical device (such as an umbilicus of a scope). This extension may improve the range of motion of a scope, allowing for a more efficient and/or effective procedure.

Figure 1:
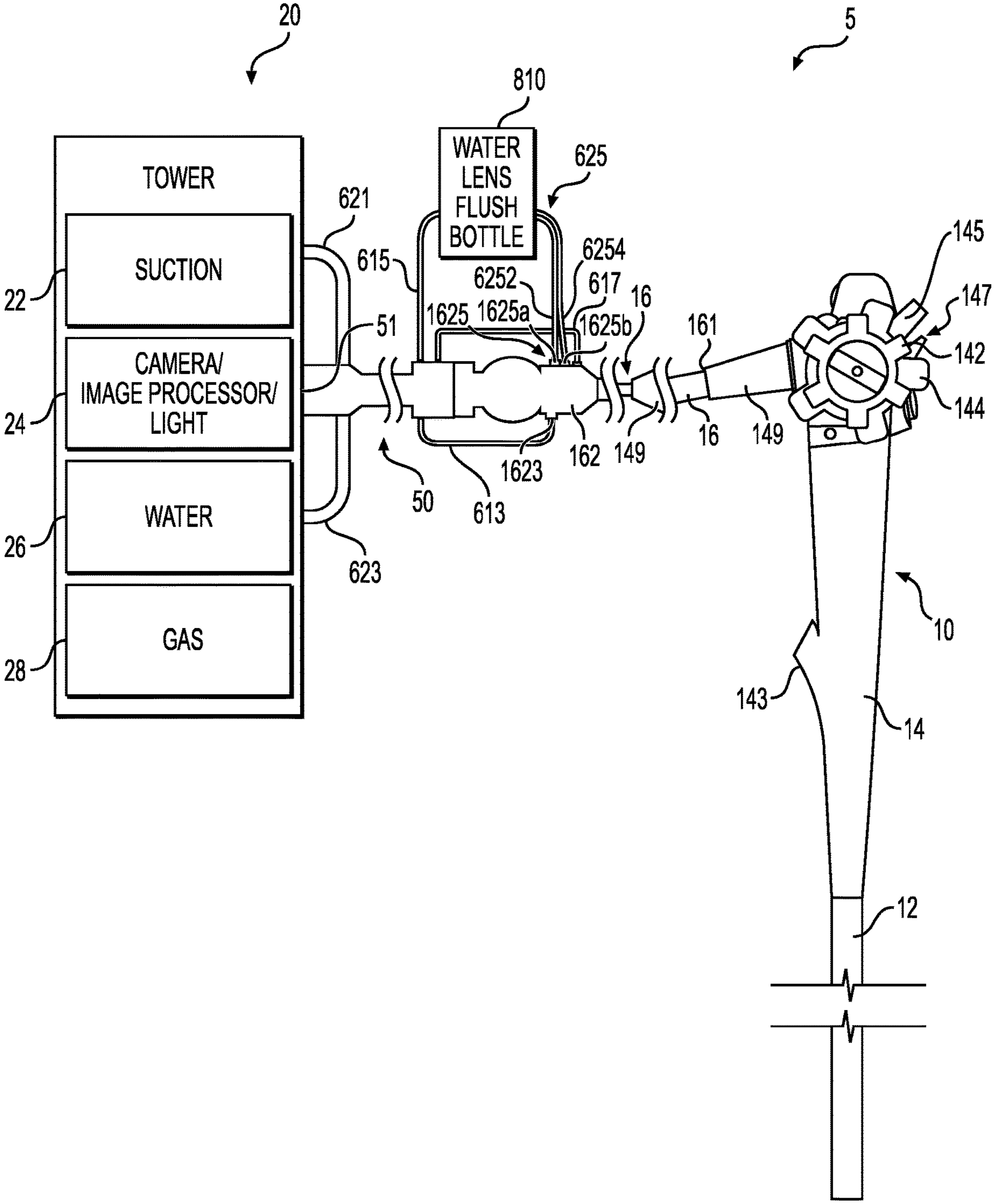
FIG. 1 is a perspective view of a medical system, according to an embodiment.

Referring to FIG. 1, a medical system 5 in accordance with one or more embodiments of this disclosure is shown. Medical system 5 may include a medical device 10, equipment supporting the medical device, such as a tower 20, and an umbilicus extension 50 extending between device 10 and tower 20. Medical device 10 is not particularly limited. Device 10 may be, as an example, any scope (e.g., bronchoscope, duodenoscope, endoscope, colonoscope, ureteroscope, etc.), catheter, tool, instrument, or the like, having a shaft/catheter 12 that extends distally from a handle 14 and an umbilicus 16 that extends proximally from the handle towards tower 20.

Shaft 12 is not particularly limited, and may be any suitable flexible shaft configured to traverse bodily lumens during a procedure. Shaft 12 may include at least one lumen (not shown) extending longitudinally from handle 14 to a distal end of shaft 12. The lumen(s) are for receiving any number of additional devices, fluids, or bodily materials, e.g., scopes, tools, instruments, cables, air, water, suction, tissue, stones, or the like.

Similarly, handle 14 is also not particularly limited, and may be any suitable medical device handle. Handle 14 may include at least one aspect, e.g., knobs 142, 144, for actuating or controlling the medical device, or any tools or devices associated with medical device. Moreover, handle 14 may include at least one port, e.g., ports 143, 145, 147, in fluid communication with lumens, including at least one working channel, of shaft 12. For example, port 143 may receive any suitable accessory device, which may extend distally through a working channel of shaft 12 and towards the distal end of the device. Ports 145 and 147 may include an air/water valve and a suction valve for controlling the flow of air/water and suction through corresponding channels of shaft 12. Handle 14 may further include an additional port 149 connected to umbilicus 16 that serves to receive, from umbilicus 149, air/water and suction, and transmit electronic signals (including light, power, and image data) between device 10 and tower 20, via umbilicus 16 and extension 50.

Umbilicus 16 is also not particularly limited, and may be any suitable flexible, elongated member or tube configured to extend between device 10 and tower 20. As noted above, a first end 161 of umbilicus 16 may connect (e.g. permanently) to a port, e.g., port 149, of handle 14. The manner in which umbilicus 16 engages port 149 is not particularly limited. Umbilicus 16 may include a proximal connector 162 which may be configured to directly (without extension 50) and indirectly (via extension 50) engage a portion of tower 20 so that device 10 may access sources of, for example, air, water (or any other fluid), suction, power, etc., as well as connect to image processing and/or viewing equipment, such as light and image sensor data. For example, a proximal end of proximal connector 162 may include a first connective feature (not shown) configured to electrically engage a first counterpart connective feature (not shown) on tower 20, which may allow for the transmission of data and/or signals between aspects of tower 20 (e.g., light source and/or a processor), and cables extending through device 10 and electronic components of device 10, such as circuit boards, image sensor, and lights. Moreover, a proximal end of proximal connector 162 may also include a second connective feature (not shown) configured to be in fluid communication with a second counterpart connective feature on tower 20, e.g., a gas source 28, which may fluidly connect gas source 28 with a respective passage extending throughout umbilicus 16. It is noted that proximal connector 162 may also include one or more protruding ports/inlets which may be in fluid communication with a respective passage of umbilicus 16.

However, as discussed throughout this disclosure, proximal connector 162 of umbilicus 16 may also be configured to connect to a distal end of extension 50, and a proximal end of extension 50 may engage tower 20, thereby lengthening the connection, i.e., extension 50 and umbilicus 16, between tower 20 and device 10. Thus, in view of the foregoing, the connective features/aspects of the proximal end of extension 50 may mirror the connective features/aspects of a proximal end of proximal connector 162, and, likewise, the connective features/aspects of the distal end of extension 50 may mirror the connective features/aspects of tower 20. This may allow for system 5 to be with or without extension 50, without any substitutions or additional features to accommodate for inconsistent connective features between tower 20 and proximal connector 162.

Umbilicus 16 may include at least one passage (not shown) housing devices and/or wiring, e.g., for imaging and lighting components, and the at least one passage may be in communication with aspects of extension 50, handle 14, and shaft 12 of medical device 10, e.g., port 149, working channel(s) of shaft 12, etc. Umbilicus 16 may further include at least one fluid passage (not shown), and in some embodiments, multiple fluid passages, for receiving a fluid, e.g., air, water, or vacuum, from tower 20. Thus, each fluid passage, e.g., an air passage, a water passage, a suction passage, etc., may be in fluid communication with aspects of extension 50, aspects of proximal connector 162 as discussed above, handle 14, and shaft 12 of medical device 10.

Tower 20 is also not particularly limited. Tower 20 may be any suitable equipment tower configured to supply device 10 with sources of vacuum/suction, e.g., a suction source 22, sources of water or other liquid, e.g., a water source 26, and sources of air/insufflation, e.g., a gas source 28, e.g., air, or a $CO_2$ source in other examples. 'Air', as used throughout this disclosure, may generally refer to any gas that may be used for insufflation or pressurizing purposes, such as air, $CO_2$, etc. Furthermore, tower 20 may include a light source, an image processor, and additional electrical auxiliary equipment (e.g. a display) configured to engage with device 10, e.g., electronics 24. Tower 20 may include a pump (not shown) associated with each of suction source 22, water source 26, and gas source 28, thereby enabling delivery of the aforementioned suction/fluids through extension 50 and towards device 10. Furthermore, it is noted that any one of the aforementioned sources 22, 24, 26, and 28 may include any suitable outlet or connective feature (not shown) that may engage with a first end of an accessory tubing, e.g., accessory tubes 621, 623, or directly engage with a connective feature, e.g., connectors 542, 544 in FIG. 2, at a proximal end of extension 50. Tower 20 may further include any additional equipment and/or devices that may be suitable, e.g., monitor(s), tubing(s), cable(s), etc. (not shown). Furthermore, the manner in which tower 20 and its various sources, equipment, etc. are arranged in not particularly limited. For example, though "tower" may imply a vertical arrangement of components/equipment used for support of device 10, the arrangement of components/equipment may be in any suitable fashion, and "tower" is not limited to a particular arrangement.

Extension 50 is a flexible elongated feature/member/shaft/tube including a first end 51, i.e., a proximal end, and a second end 52, i.e., a distal end. The length of extension 50 is not particularly limited, and may be any suitable length, for example, from approximately 6 feet to approximately 30 feet. As shown in FIG. 1, first end 51 may engage one or more aspects of tower 20, e.g., electronics 24, and second end 52 may engage second end 162 of umbilicus 16. Thus, extension 50 may extend between umbilicus 16 and tower 20, thereby lengthening the connection between device 10 and tower 20. Such lengthening may improve the range of motion of device 10, as well as allow for more effective operation of additional devices or equipment (such as a boom arm) configured to reposition or manipulate umbilicus 16 and extension 50, in an attempt to further the improve range of motion of device 10. In other examples, a plurality of extensions may be linked or coupled to one another via any suitable connective means, thereby further lengthening the connection between device 10 and tower 20. It is noted that the material of extension 50 is not particularly limited, and may be any suitable material that is flexible and suitable for fluid delivery to and from a patient.

Extension 50 may include one or more channels, e.g., channels 531, 533, 535, 537, extending throughout extension 50 or at least a portion thereof. Furthermore, extension 50 may include any number of connective features, inlets, outlets, etc., each of which may engage umbilicus 16, tower 20, or an accessory tubing or catheter, e.g., tubes 613, 615, 617, 621, 623. Each of the aforementioned connective features, inlets, and outlets may include a passage in communication with the one or more channels, e.g., channels 531, 533, 535, 537, extending throughout extension 50. Each of channels 531, 533, 535, and 537 may be configured to provide passage of electronic cables and/or bundles, air, suction, and water for irrigation, respectively.

First Channel 531

Figure 2:
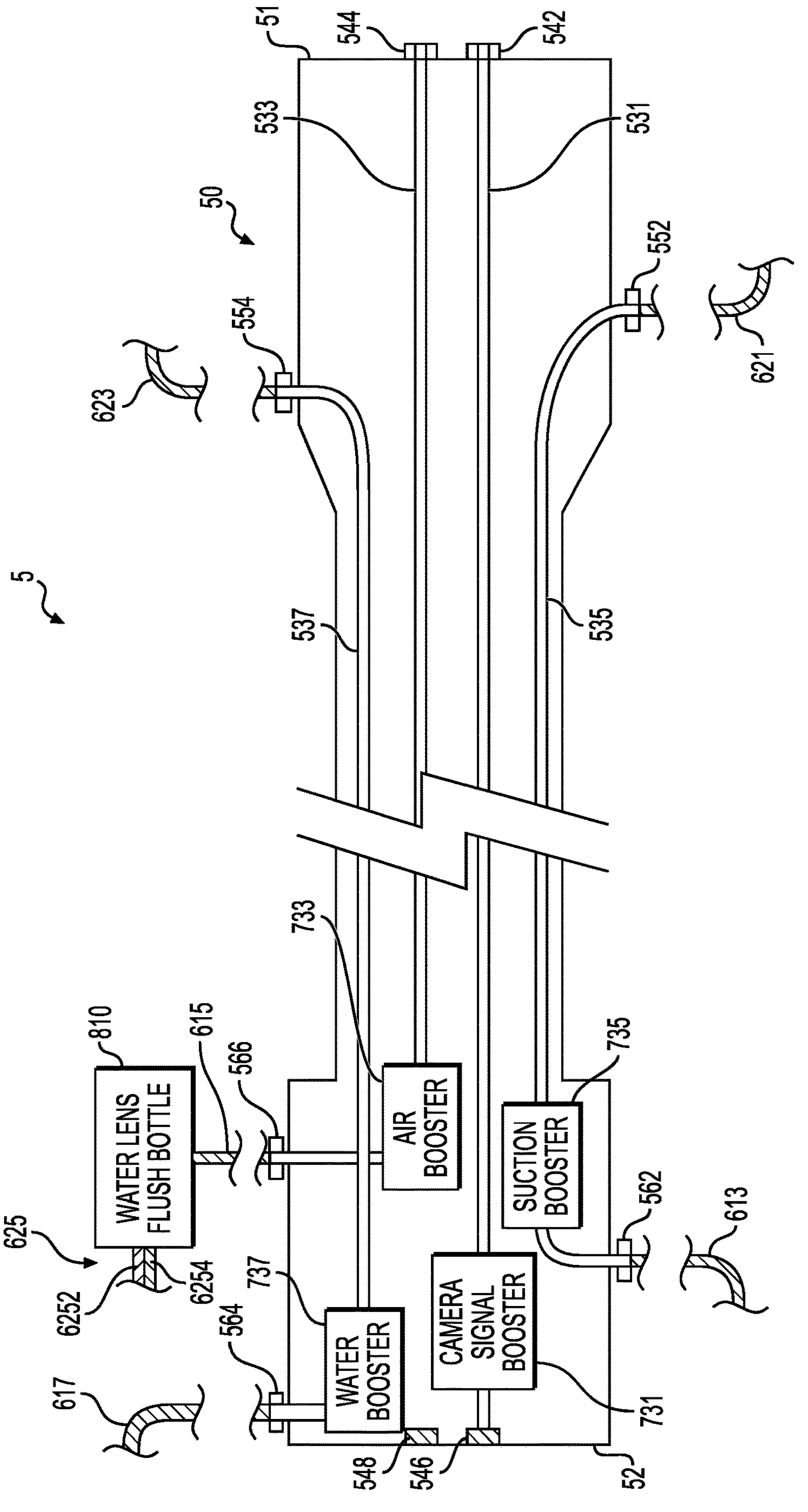
FIG. 2 is a cross-sectional view of the umbilicus extension of FIG. 1.

For example, as shown in FIG. 2, extension 50 includes a first connector 542, a second connector 546, and first channel 531 extending therebetween. First connector 542 protrudes proximally from first end 51, but is not limited thereto. First connector 542 is not particularly limited, and may be any suitable connector configured to engage with a counterpart connective feature (not shown) that may be present on an aspect of tower 20 (shown in FIG. 1). For example, first connector 542 may be an electrical connector (or a plurality of electrical connectors) configured to engage an electrical connective feature (or a plurality of electrical connective features) present on electronics 24 (shown in FIG. 1), thereby establishing an electrical connection(s), e.g., an electrical contact connection. First connector 542 also connects with one or more cables or electrical bundles (not shown), e.g., fiber optic cables, extending through first channel 532 towards second connector 546, for conveying camera signals, electrical signals, light, data, etc.

Second connector 546 is recessed proximally inwards from second end 52, but is not limited thereto. Second connector 546 is also not particularly limited, and may be any suitable connector, e.g., a female connector, configured to engage with a counterpart connective feature (not shown), e.g., a male connector, that may be present on proximal connector 162 of umbilicus 16 (shown in FIG. 1). As noted above, second connector 546 may include a passage linking first channel 531 with a respective lumen (not shown) extending through umbilicus 16 and device 10. Furthermore, as previously noted, first connector 542 may be identical or similar to the counterpart connective feature present on a proximal end of proximal connector 162, and second connector 546 may be identical or similar to the counterpart connective feature present on electronics 24.

First channel 531 is not particularly limited, and may be of any suitable dimension providing passage to one or more cables, electrical bundles, etc. conveying camera signals, light, data, etc. from electronics 24 of tower 20 to device 10. It is noted that first channel 531 may further include a signal booster 731 engaging the one or more cables and/or electrical bundles. Signal booster 731 is not particularly limited, and may be any suitable booster, e.g., coaxial cables, amplifier, etc., configured to boost or enhance signal strength, e.g., camera signals. The location of signal booster 731 along a length of first channel 531 is also not particularly limited. For example, as shown in FIG. 2, signal booster 731 may be located within a distal portion of first channel 531. Given that the presence of extension 50 in medical system 5 necessitates a longer transmission path than a standard umbilicus, signal booster 731 may help maintain signal strength and fidelity throughout the connection, i.e., extension 50 and umbilicus 16, between tower 20 and device 10. It is noted that signal booster 731 may be with or without a control mechanism, as signal booster 731 may be on or off in accordance with the components of electronics 24. In other exemplary embodiments, in which device 10 includes a plurality of imaging devices or cameras and corresponding imaging streams (e.g., cables, electrical bundles, etc), first channel 531 (or additional channels) may include additional signal boosters 731. For example, each imaging stream between the cameras of device 10 and electronics 24 may be supplemented by an individual signal booster 731. In such embodiments, each signal booster 731 may be operational (on/off) independent of the other signal boosters. In some other exemplary embodiments, in which device 10 includes a plurality of imaging devices or cameras but a consolidated imaging stream between said cameras and electronics 24, said consolidated imaging stream may be supplemented by a single signal booster 731, similar to as shown in FIG. 2 (and FIG. 3), but not limited thereto.

Second Channel 533

Extension 50 also includes a third connector 544, a recess 548, a first outlet 566, and a second channel 533 extending between third connector 544 and first outlet 566. Third connector 544 protrudes proximally from first end 51, but is not limited thereto. Third connector 544 is not particularly limited, and may be any suitable connector configured to engage with a counterpart connective feature (not shown) that may be present on an aspect of tower 20. For example, third connector 544 may be a connective feature, e.g., male connector, configured to engage a counterpart connective feature, e.g., female connector, of gas source 28 (shown in FIG. 1). As noted above, third connector 544 includes a passage allowing for fluid communication between gas source 28 and second channel 533.

Recess 548 is recessed proximally inwards from second end 52, but is not limited thereto. Recess 548 is not particularly limited, and may be any suitable indentation, configured to receive or accommodate a counterpart connective feature (not shown), that may be present on proximal connector 162 of umbilicus 16. Recess 548 is not in communication with second channel 533, and does not provide passage of air to the counterpart connective feature of proximal connector 162. Rather, recess 548 may function to accommodate for the presence of said connective feature of proximal connector 162, which otherwise would directly engage tower 20 without extension 50. In some examples, recess 548 may also function as a seal, e.g., a sealing alcove, thereby inhibiting any leakage of fluid to or from extension 50 or proximal connector 162. As previously noted, third connector 544 may be identical or similar to the counterpart connective feature present on a proximal end of proximal connector 162, and recess 548 may be of identical or similar shape and dimensions to the counterpart connective feature present on gas source 28.

First outlet 566 protrudes radially outwards from a distal portion of extension 50. First outlet 566 is not particularly limited, and may be any suitable outlet configured to engage with an accessory tubing, e.g., tube 615. As noted above, first outlet 566 includes a passage linking second channel 533 with a respective lumen of tubing 615. Tubing 615 and its engagement with a water lens flush bottle 810 is discussed in further detail below.

Second channel 533 is not particularly limited, and may be of any suitable dimension providing passage to a gas, e.g., air, from gas source 28. Second channel 533 may also provide passage to other fluids, such as $CO_2$, which may be stored in a different source from gas source 28. It is noted that second channel 533 may further include an air booster 733. Air booster 733 is not particularly limited, and may be any suitable booster or pump, i.e., any mechanism that increases pressure of fluid, e.g., air, $CO_2$, etc. Thus, air booster 733 may be any suitable booster or pump configured to pressurize the fluid passing through second channel 533. The location of air booster 733, as shown in FIG. 2, may be located within a distal portion of second channel 533, e.g., proximate to second (distal) end 52. Thus, air booster 733 may be located at an intermediary position within the connection, i.e., extension 50 and umbilicus 16, between tower 20 and device 10. Such positioning of air booster 733 may help maintain consistent air pressure throughout the connection between tower 20 and device 10, as air booster 733 may maintain pressure or help restore any loss of pressure occurring through extension 50, from the pressure by which air is initially delivered from gas source 28.

Medical system 5 may further include a secondary water source, e.g., lens flush bottle 810, which may be in fluid communication with gas source 28, to pressurize the water for any suitable purpose, e.g., lens flushing. For example, as shown in FIG. 2, lens flush bottle 810 may be in connection with tubing 615, and downstream of air booster 733. Thus, second channel 533 may provide passage of pressurized air towards outlet 566, through a lumen of tubing 615 coupled to outlet 566, and to lens flush bottle 810. Lens flush bottle 810 may include any suitable valve or outlet (not shown), to which a tubing 625 may be coupled, which allows for pressurized air and water to be routed to a port/inlet of proximal connector 162, e.g., a port 1625, via tubing 625. Tubing 625 may include more than one channel. For example, tubing 625 may include a first passage 6252 configured to receive and route pressurized air from lens flush bottle 810 to proximal connector 162, and a second passage 6254 configured to receive and route pressurized water from lens flush bottle 810 to proximal connector 162. A distal or downstream portion of tubing 625 may fork or split between first passage 6252 and second passage 6254 so that first passage 6252 may be in fluid communication with a first inlet 1625*a* of port 1625, and second passage 6254 may be in fluid communication with a second inlet of port 1625*b*, as shown in FIG. 1. Pressurized air and water may then be routed from first inlet 1625*a* and second inlet 1625*b* of port 1625 to a respective fluid lumen or lumens, e.g., a pressurized water lumen and a pressurized air lumen, of umbilicus 16, and to a channel or channels of shaft 12 thereafter. As a result of such configuration, air from gas source 28 may be pressurized via air booster 733, and 1) vented to atmosphere out of port 145 via second channel 533, first passage 6252, and a respective lumen of umbilicus

16, or 2) delivered to shaft 12 via second channel 533, first passage 6252, and a respective lumen of umbilicus 16 when blocked from escape by user input at port 145, or 3) delivered to lens flush bottle 810 via second channel 533 when redirected by user input at port 145, thereby pressurizing the water of bottle 810 for lens flushing purposes. A user may direct air flow via one of the three options noted above by manipulation of a valve (not shown) positioned in port 145 of device 10.

Medical system 5 may also include a second tower, surface, holder, etc. (not shown) configured to hold lens flush bottle 810 at the intermediary junction between tower 20 and device 10. Medical system 5 may further include a control mechanism (not shown) by which air booster 733 of extension 50 may be actuated or controlled. For example, air booster 733 may include a high-amperage shutoff controller that will maintain air booster 733 in an operating ('on') state, unless above a high-amperage is demanded of air booster 733. Operating-amperage may be defined at and between low and high amperages of the following two conditions: 1) when the valve or outlet in port 145 is venting pressurized air to the atmosphere, the amperage demand may be low; and 2) when the valve or outlet in port 145 is routing air to pressurize the water lens flush bottle for lens flush, the amperage demand may be high. Thus, amperage values at and between these conditions or thresholds may be instances in which the valve or outlet in port 145 is routing pressurized air to device 10, and such instances may be when the controller remains 'on'. However, it is noted that the control mechanism of air booster 733 is not limited to the exemplary controller discussed above, and may be via any suitable means.

Third Channel 535

Extension 50 also includes a first inlet 552, a second outlet 562, and third channel 535 extending therebetween. First inlet 552 protrudes radially outwards from a proximal portion of extension 50. First inlet 552 is not particularly limited and may be any suitable inlet configured to engage with an accessory tubing, e.g., tubing 621. As noted above, first inlet 552 includes a passage linking third channel 535 with a respective lumen of tubing 621, which in turn may be in connection with an aspect of tower 20, e.g., suction source 22 (shown in FIG. 1).

Second outlet 562 protrudes radially outwards from a distal portion of extension 50. Second outlet 562 is not particularly limited, and may be any suitable outlet configured to engage with an accessory tubing, e.g., tube 613. As noted above, second outlet 562 includes a passage linking third channel 535 with a respective lumen of tubing 613, which in turn may be in connection with device 10 via a port/inlet of proximal connector 162, e.g., port 1623, and a respective lumen of umbilicus 16. Thus, first inlet 552 and second outlet 562 may allow for fluid communication between suction source 22 and device 10.

Third channel 535 is not particularly limited, and may be of any suitable dimension providing passage to suction from suction source 22. Third channel 535 may further include a suction booster 735. Suction booster 735 is not particularly limited, and may be any suitable booster or pump, i.e., any mechanism that increases pressure of fluid. Thus, suction booster 735 may be any suitable booster or pump configured to pressurize the suction. The location of suction booster 735, as shown in FIG. 2, may be located within a distal portion of third channel 535, e.g., proximate to second (distal) end 52. Thus, suction booster 735 may be located at an intermediary position within the connection, i.e., extension 50 and umbilicus 16, between tower 20 and device 10. Such positioning of suction booster 735 may help maintain a consistent suction pressure throughout the connection between tower 20 and device 10, as suction booster 735 may maintain pressure or help restore any loss of pressure occurring through extension 50, from the pressure by which suction is initially applied from suction source 22.

Medical system 5 may further include a control mechanism (not shown) by which suction booster 735 of extension 50 may be actuated or controlled. For example, suction booster 735 may include a high-amperage shutoff controller that will maintain suction booster 735 in an operating ('on') state, unless a high-amperage is demanded of suction booster 735. High-amperage may stem from suction simply not being used; when suction is used and routed from suction source 22, through third channel 535, towards device 10, the amperage demanded from suction booster 735 may be lower and suction booster 735 may remain operating. Suction source 22 may be in the 'on' state during the entirety of a procedure, and suction may be controlled via a valve (not shown) in port 147. For example, the valve may be placed in a first position via user input, in which the valve is nominally blocked off, although it may suction some air from the atmosphere. This would draw high amperage, and suction booster 735 would not be needed under this condition. The valve may also be placed in a second position via user input, in which the atmosphere is closed off, and a connection is established to pull suction through shaft 12. This would be a relatively lower amperage condition, and suction booster 735 would be needed in this instance. However, it is noted that the control mechanism of suction booster 735 is not limited to the exemplary controller discussed above, and may be via any suitable means.

Fourth Channel 537

Extension 50 also includes a second inlet 554, a third outlet 564, and fourth channel 537 extending therebetween. Second inlet 554 protrudes radially outwards from a proximal portion of extension 50. Second inlet 554 is not particularly limited and may be any suitable inlet configured to engage with an accessory tubing, e.g., tubing 623. As noted above, second inlet 554 includes a passage linking fourth channel 537 with a respective lumen of tubing 623, which in turn may be in connection with an aspect of tower 20, e.g., water source 26 (shown in FIG. 1).

Third outlet 564 protrudes radially outwards from a distal portion of extension 50. Third outlet 564 is not particularly limited, and may be any suitable outlet configured to engage with an accessory tubing, e.g., tube 617. As noted above, third outlet 564 includes a passage linking fourth channel 537 with a respective lumen of tubing 617, which in turn may be in connection with device 10 via a port/inlet of proximal connector 162, e.g., port 1627, and a respective lumen of umbilicus 16. Thus, second inlet 554 and third outlet 564 may allow for fluid communication between water source 26 and device 10.

Fourth channel 537 is not particularly limited, and may be of any suitable dimension providing passage to water from water source 26. Fourth channel 537 may further include a water/fluid booster 737. Water booster 737 is not particularly limited, and may be any suitable booster or pump, i.e., any mechanism that increases pressure of fluid. Thus, water booster 737 may be configured to pressurize the water (or fluid) passing therethrough. The location of water booster 737, as shown in FIG. 2, may be located within a distal portion of fourth channel 537, e.g., proximate to second (distal) end 52. Thus, water booster 737 may be located at an intermediary position within the connection, i.e., extension 50 and umbilicus 16, between tower 20 and device 10.

Such positioning of water booster 737 may help maintain water flow at a consistent pressure throughout the connection between tower 20 and device 10, as water booster 737 may maintain pressure or help restore any loss of pressure occurring through extension 50, from the pressure by which water is initially delivered from water source 26.

Medical system 5 may further include a control mechanism (not shown) by which water booster 737 of extension 50 may be actuated or controlled. For example, a switch, button, or pedal, e.g., a foot pedal, may be in connection, via any suitable means, e.g., a Y-cable, with both water booster 737 and the pump (not shown) in engagement with water source 26 of tower 20. Thus, the actuation of said control mechanism may relay a signal to both the pump of water source 26 and water booster 737 simultaneously, allowing for fluid delivery from tower 20 to device 10. In other examples, water booster 737 may include a sensor, e.g., a flow sensor, such that when flow of water within a certain flow rate range (greater than no-flow, but slower than necessary to reach second end 52 of extension 50 in a useful timeframe) is detected, water booster 737 is turned 'on' to an operating state. If flow is outside of the range, then water booster 737 remains 'off' in a non-operating state. However, it is noted that the control mechanism of water booster 737 is not limited to the exemplary mechanisms discussed above, and may be via any suitable means.

Thus, as shown in FIG. 2, extension 50 may have a plurality of boosters, e.g., air booster 733, suction booster 735, water booster 737, that are downstream of the connections between extension 50 and equipment of tower 20, proximate to second (distal) end 52 of extension 50. Extension 50 may further include additional features or accessories. In some examples, extension 50 may further include one or more seals at second end 52 to inhibit or minimize any leakage of fluid, e.g., water, air, at second end 52. The seals are not particularly limited, and may be adhered to an exterior or interior surface of extension 50.

Figure 3:
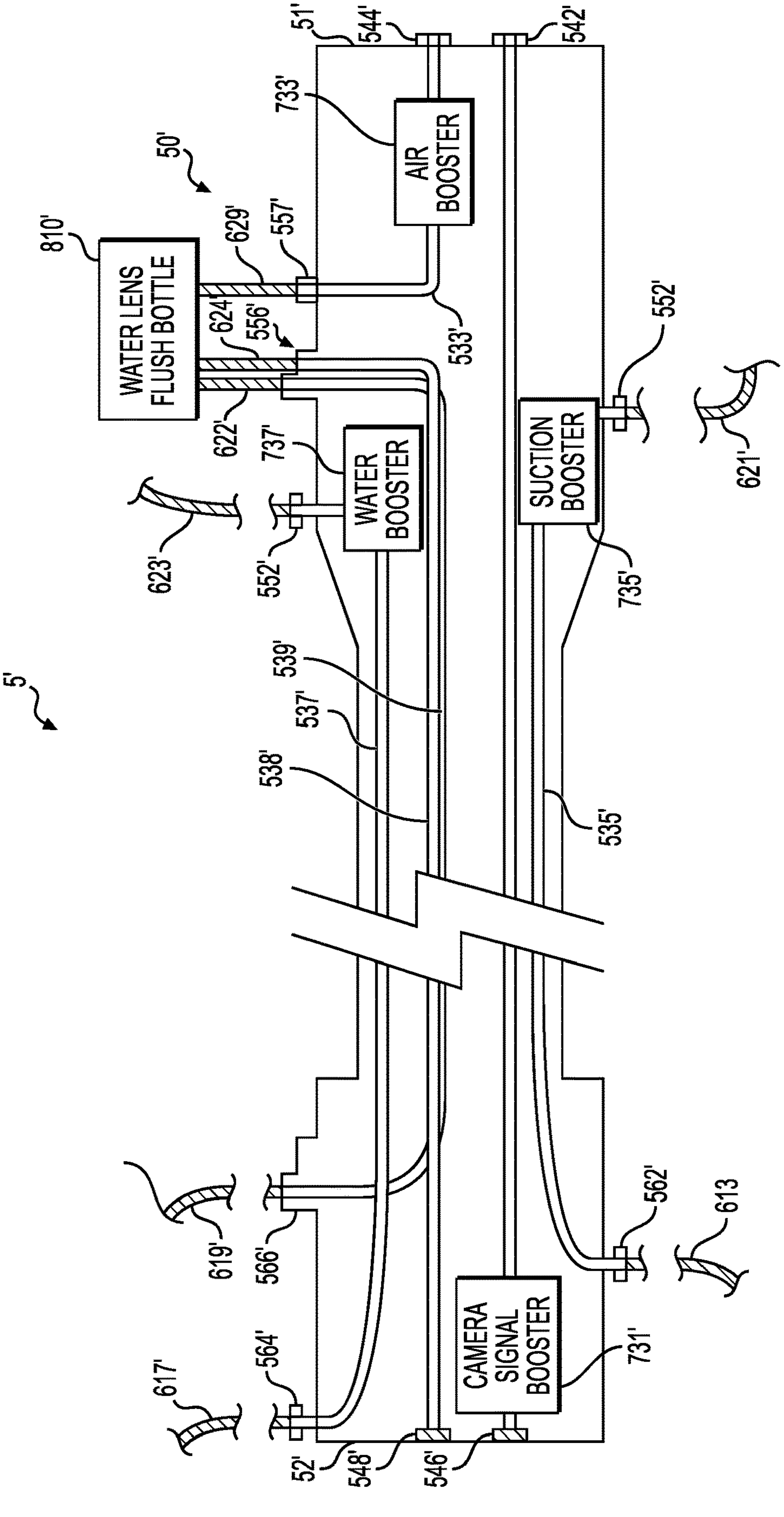
FIG. 3 is a cross-sectional view of an umbilicus extension, according to another embodiment.

Referring to FIG. 3, another embodiment of extension 50' of system 5' is described below. Extension 50' is similar to extension 50 in many respects. Like reference numerals, e.g., 51' and 51, refer to like parts. Differences between extension 50' and 50 are further described below.

Unlike extension 50, air booster 733', suction booster 735', and water booster 737' may be located within proximal portions of their respective channels, proximate to first (proximal) end 51' and tower 20 (shown in FIG. 1). Thus, air booster 733', suction booster 735', and water booster 737' may be located at a proximal position within the connection, i.e., extension 50' and umbilicus 16 (shown in FIG. 1), between tower 20 and device 10 (shown in FIG. 1). Such upstream positioning of the aforementioned boosters may necessitate pressurizing the respective fluids and suction to a greater degree than typical tower-to-device connections, as additional pressure may be needed to convey the respective fluids and suction throughout the lengthened connection, i.e., extension 50.

As shown in FIG. 3, extension 50' includes a second channel 533' extending between third connector 544' and a proximal outlet 557', as well as a fifth channel 538' and a sixth channel 539' extending between a proximal inlet 556' and a fourth connector 548'.

Second channel 533' may extend distally from third connector 544', through air booster 733', to a proximal outlet 557'. As previously noted, third connector 544' is not particularly limited, and may be any suitable connector, e.g., male connector, configured to engage a counterpart connective feature, e.g., female connector, of gas source 28. Third connector 544' includes a passage allowing for fluid communication between gas source 28 and second channel 533'. Second channel 533' may extend towards proximal outlet 557', which may extrude radially outwards at a proximal portion of extension 50'. Proximal outlet 557' is not particularly limited and may be any suitable outlet configured to engage with at least one accessory tubing, e.g., tubing 629'. Proximal outlet 557' may include a passage linking second channel 533' with a respective lumen of tubing 629'. Tubing 629' may be in connection with lens flush bottle 810', and thus may provide passage of pressurized air to lens flush bottle 810'.

Extension 50' further includes a fifth channel 538' extending between proximal inlet 556' and fourth connector 548'. Proximal inlet 556' may further include a first passage linking fifth channel 538' with a respective lumen of tubing 624' engaging proximal inlet 556'. Tubing 624' may also be in connection with lens flush bottle 810', thereby providing passage of pressurized fluid, e.g., pressurized air, from lens flush bottle 810', through a lumen of tubing 624', to fifth channel 538'. Fourth connector 548' is not particularly limited, and may be any suitable connector, e.g., a female connector, configured to engage a counterpart connective feature, e.g., a male connector, of proximal connector 162. Fourth connector 548' includes a passage allowing for fluid communication between fifth channel 538' and a respective lumen of umbilicus 16. Thus, pressurized air from lens flush bottle 810' may pass through fifth channel 538' to a lumen of umbilicus 16, via the passage of fourth connector 548'.

Extension 50' further includes a sixth channel 539' extending between proximal inlet 556' and distal outlet 566'. Proximal inlet 556' may further include a second passage linking sixth channel 539' with a respective lumen of tubing 622' engaging proximal inlet 556'. Tubing 622' may also be in connection with lens flush bottle 810', thereby providing passage of pressurized fluid, e.g., pressurized water, from lens flush bottle 810', through a lumen of tubing 622', to sixth channel 539'. Distal outlet 566' protrudes radially outwards from a distal portion of extension 50'. Distal outlet 566' is not particularly limited and may be any suitable outlet configured to engage with at least one accessory tubing, e.g., tubing 619', which may engage an inlet/port (not shown) of proximal connector 162. Distal outlet 566' includes a passage linking sixth channel 539' with a respective lumen of tubing 619'. Thus, pressurized water from lens flush bottle 810' may pass through sixth channel 539' to a lumen of umbilicus 16, via the passage of distal outlet 566' and lumen of tubing 619'.

As a result of such configuration, air from gas source 28 (or a $CO_2$ source) may be pressurized via air booster 733', and 1) vented to the atmosphere out of port 145 via fifth channel 538' and a respective lumen of umbilicus 16, or 2) delivered to shaft 12 via fifth channel 538' and a respective lumen of umbilicus 16 when blocked from escape by user input at port 145, or 3) delivered to lens flush bottle 810' via second channel 533 and tubing 629' when redirected by user input at port 145, thereby pressurizing the water of bottle 810' for lens flushing purposes. A user may direct air flow via one of the three options noted above by manipulation of a valve (not shown) positioned in port 145 of device 10. Water from lens flush bottle 810' may be routed towards device 10' via sixth channel 539', which may be in fluid communication with tubing 619', and in turn, proximal connector 162, a respective lumen of umbilicus 16, and device 10. Given the proximal location of air booster 733' within extension 50', as well as proximal outlet 556', lens flush bottle 810' may be on or coupled to tower 20 (not shown in FIG. 3) in medical system 5'. This may minimize infrastructure, relative to system 5, as system 5, shown in FIG. 2, may further require a second tower, surface, holder, etc. for holding lens flush bottle 810 at an intermediary junction between tower 20 and device 10.

As mentioned above, first end 51', second end 52', first connector 542', second connector 546', channel 531, signal booster 731, first inlet 552', tubing 623', a second outlet 562', tubing 613', third channel 535', a second inlet 554', tubing 621', third outlet 564', tubing 617', and fourth channel 537' are the same as or similar to the corresponding elements shown in FIG. 2.

Figure 4A:
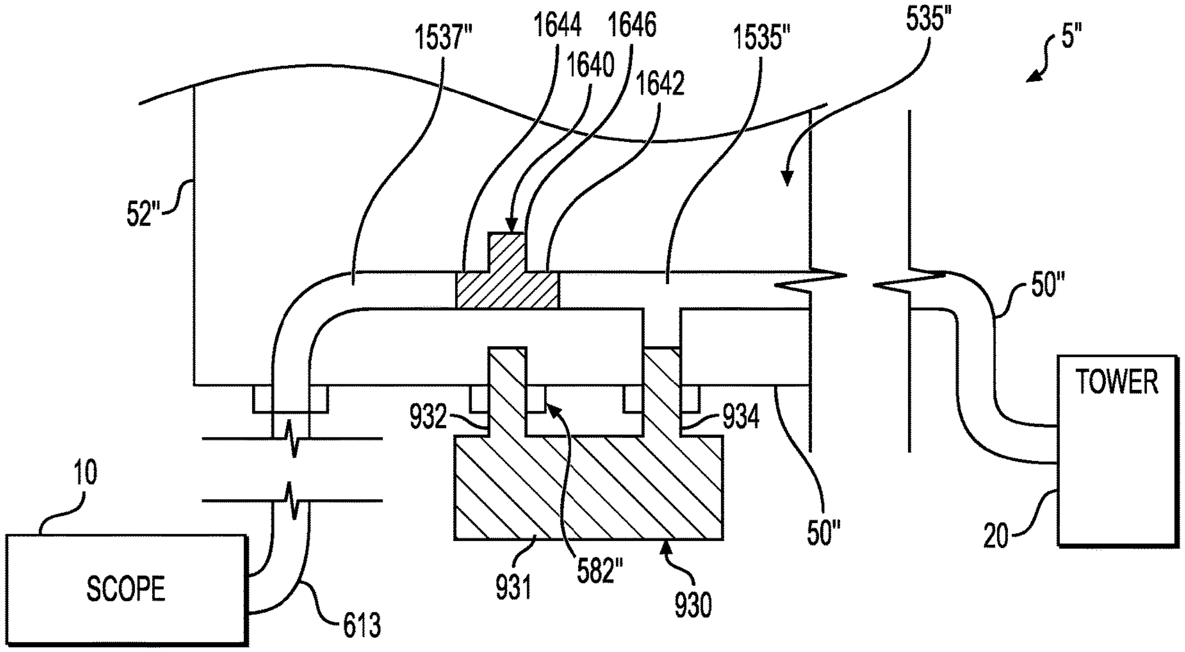
FIGS. 4A-4B are partial cross-sectional views of a medical system according to another embodiment.
Figure 4B:
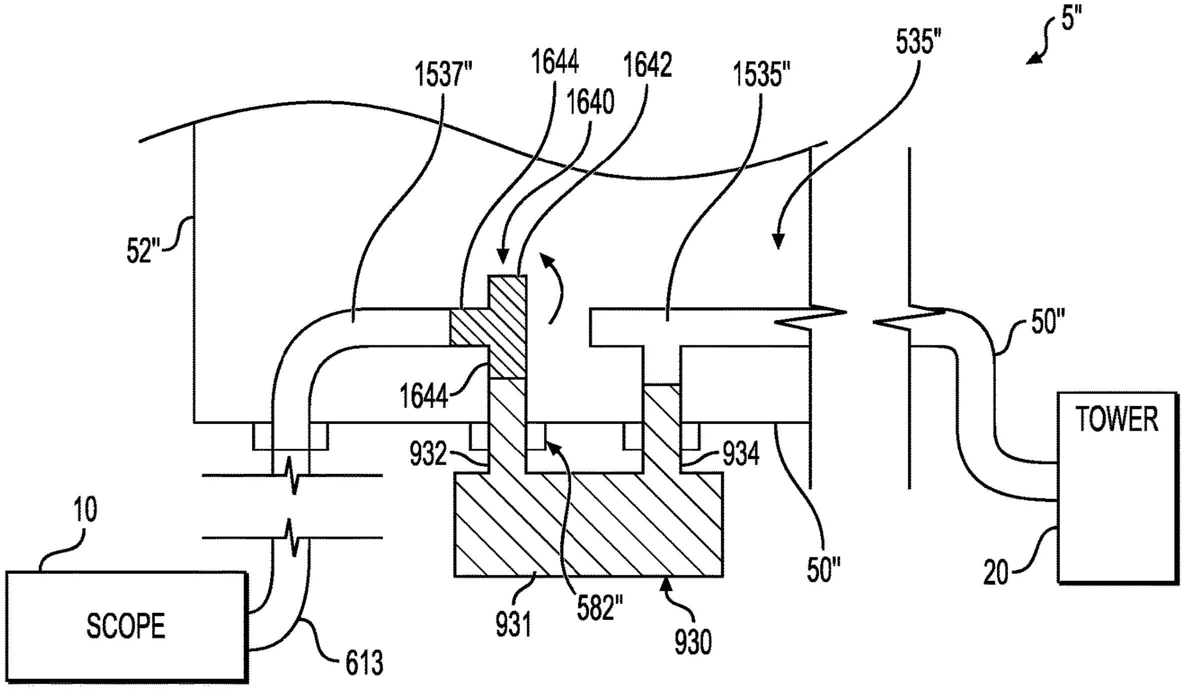

Referring to FIGS. 4A-4B, another embodiment of extension 50" of medical system 5" is described below. Extension 50" is similar to extension 50 in many respects. Like reference numerals, e.g., 50" and 50, refer to like parts.

As shown in FIGS. 4A and 4B, a trap 930 may be coupled to extension 50". Trap 930 may be any suitable compartment or housing including a cavity 931, which may be configured to receive and hold fluids, tissues, materials, objects, stones, etc. that have been drawn from a patient via suction. Trap 930 further includes a first leg defining a first lumen 932 and an adjacent second leg defining a second lumen 934, both lumens 932 and 934 being in fluid communication with cavity 931. First lumen 932 and second lumen 934 extend perpendicularly relative to length of cavity 931, and, as shown in FIGS. 4A and 4B, extend through a port 582" of extension 50", thereby coupling trap 930 to extension 50".

Port 582" includes a pair of adjacent openings or passages. Each of the aforementioned openings may be configured to receive a leg of trap 930, such that first lumen 932 and second lumen 934 may extend radially inwards of extension 50", towards third channel 535". Port 582" may be positioned on a distal portion of extension 50", proximate to second end 52". However, the location of port 582" is not limited thereto.

Third channel 535" may extend between a proximal inlet (not shown) and outlet 522". Unlike third channel 535 of extension 50, third channel 535" may include a plurality of segments, e.g., first portion 1535", a branched connector 1640, and a second portion 1537", all of which are aligned with one another, thereby defining the suction flow path between tower 20 and device 10.

As shown in FIGS. 4A-4B, first portion 1535" includes a branch extending radially outwards, towards a first opening 5821" of a port 582". Branched connector 1640 may be a three-way connective feature including a first branch 1642, a second branch 1644, and a third branch 1646. Branched connector 1640 may be rotatable clockwise or counter-clockwise approximately 90 degrees about a central axis, i.e., the point from which first branch 1642, second branch 1644, and third branch 1646 branch away from one another. Thus, branched connector 1640 may transition between a first position, as shown in FIG. 4A, and a second position, as shown in FIG. 4B, via rotation. The manner by which connector 1640 may be rotated is not particularly limited, and may be by any suitable mechanism.

In the first position, first branch 1642 may be in fluid communication with a distal end of first portion 1535", and second branch 1644 may be in fluid communication with a proximal end of second portion 1537". Third branch 1646, meanwhile, may extend radially inwards of extension 50", and may not be in fluid communication with an aspect of third channel 533'. It is noted, when connector 1640 is in the first position, the suction path may travel from scope 10, through third channel 535", bypassing trap 930.

In the second position, third branch 1646 may be in fluid communication with a proximal end of second portion 1537" and second branch 1644 may be in fluid communication with second lumen 932 of trap 930. First branch 1642, meanwhile, may extend radially inwards of extension 50", and may not be in fluid communication with an aspect of third channel 535". When connector 1640 is in the second position, the suction path may travel from scope 10 to trap 930 (via second portion 1537", connector 1640, and first lumen 932) and from trap 930 to tower 20 (via second lumen 934 and first portion 1535"). Thus, a user may transition branched connector 1640 to the aforementioned second position to collect any materials suctioned from a patient into trap 930.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:
- a scope including a shaft, a handle, and a first tube extending from the handle;
- medical equipment including a processor and a first fluid source; and
- a second tube comprising:
  - a first end including a first connector engaging the processor, and a second connector engaging the first fluid source,
  - a second end including a third connector engaging the first tube,
  - a first channel configured to convey data from the processor to the scope, wherein the first channel extends between the first connector and the third connector, and
  - a second channel configured to convey fluid from the first fluid source to the scope, wherein the second channel extends between the second connector and a first fluid outlet of the second tube,
  - wherein the second channel includes a first pump configured to pressurize the fluid passing through the second channel, the first pump being closer to either the second end of the second tube or the first end of the second tube.

2. The medical system of claim 1, wherein the first channel includes a booster configured to boost the transmission of data from the processor to the scope, wherein the booster is closer to the second end of the second tube than the first end of the second tube.

3. The medical system of claim 1, wherein the first pump is closer to the second end of the second tube than the first end of the second tube.

4. The medical system of claim 3, wherein the first pump is configured to at least restore a loss of fluid pressure by which the fluid was initially conveyed from the first fluid source to the second channel.

5. The medical system of claim 3, further comprising a secondary water source downstream of the first pump, wherein the secondary water source is located at a junction between the first end and the second end of the second tube,
wherein the first fluid source is air, and wherein the secondary water source is in fluid communication with the second channel, so that the first pump is configured to pressurize the secondary water source.

6. The medical system of claim 1, wherein the first pump is closer to the first end of the second tube than the second end of the second tube.

7. The medical system of claim 6, further comprising a secondary water source downstream of the first pump, wherein the secondary water source is located at a same location as the medical equipment, wherein the first fluid source is air, and wherein the secondary water source is in fluid communication with the second channel, so that the first pump is configured to pressurize the secondary water source.

8. The medical system of claim 1, wherein the medical equipment further includes a second fluid source, and wherein the second tube further comprises a third channel configured to convey fluid from the second fluid source, wherein the third channel is in fluid communication with the second fluid source, and wherein the third channel includes a second pump configured to pressurize the fluid passing through the third channel.

9. The medical system of claim 8, wherein the third channel extends between a first fluid inlet of the second tube and a second fluid outlet of the second tube, and the medical system further comprises a first tubing extending between the first fluid inlet and the second fluid source, and a second tubing extending between the second fluid outlet and the scope.

10. The medical system of claim 9, wherein the medical equipment further includes a suction source, and wherein the second tube further comprises a fourth channel configured to convey fluid to the suction source, wherein the fourth channel is in fluid communication with the suction source, and wherein the fourth channel includes a third pump configured to pressurize the fluid passing through the third channel.

11. The medical system of claim 10, wherein the fourth channel extends between a second fluid inlet of the second tube and a third fluid outlet of the second tube, and the medical system further comprises a third tubing extending between the second fluid inlet and the suction source, and a fourth tubing extending between the third fluid outlet and the scope.

12. The medical system of claim 11, wherein fluid of the second fluid source is water.

13. The medical system of claim 11, wherein the first pump, the second pump, and the third pump are closer to the second end of the second tube than the first end of the second tube.

14. The medical system of claim 1, wherein the second end of the second tube includes a seal configured to inhibit leakage of fluid from the first fluid source from the second end.

15. A medical system, comprising:

a scope including a shaft, a handle, and a first tube extending from the handle;

medical equipment including a processor and a first fluid source; and a second tube comprising:

a first end including a first connector engaging the processor, and a second connector engaging the first fluid source, a second end including a third connector engaging the first tube, an electronics channel extending between the first connector and the third connector, the electronics channel configured to convey data from the processor to the scope, a fluid channel extending between the second connector and a first fluid outlet of the second tube, a first pump configured to pressurize fluid passing through the fluid channel, wherein the first pump is positioned nearer to the second end of the second tube than the first end of the second tube, and a secondary water source downstream of the first pump, wherein the secondary water source is located at a junction between the first end and the second end of the second tube.

16. The medical system of claim 15, wherein the electronics channel includes a signal booster, wherein the signal booster is positioned nearer to the second end of the second tube than the first end of the second tube.

17. The medical system of claim 15, wherein the fluid channel is a first fluid channel, wherein the second tube further includes a second fluid channel extending from a fourth connector at the first end to an outlet, wherein the second fluid channel includes a second pump configured to pressurize fluid passing through the second fluid channel, wherein the second pump is positioned along the second fluid channel and is positioned nearer to the second end than the first end.

18. A medical system, comprising:

a scope including a shaft, a handle, and a first tube extending from the handle;

medical equipment including a processor and a first fluid source; and a second tube comprising:

a first end including a first connector engaging the processor, and a second connector engaging the first fluid source, a second end including a third connector engaging the first tube, an electronics channel extending between the first connector and the third connector, the electronics channel configured to convey data from the processor to the scope, a first fluid channel extending between the second connector and a first fluid outlet of the second tube, the first fluid channel including a first pump positioned along the first fluid channel and configured to pressurize fluid passing through the first fluid channel, a suction channel extending between an inlet positioned proximate the second end and a second fluid outlet positioned proximate the first end, the suction channel including a second pump positioned along the suction channel and configured to pressurize fluid passing through the suction channel.

19. The medical system of claim 18, further comprising: a suction source, wherein the outlet of the suction channel is fluidly coupled to the suction source.

20. The medical system of claim 18, wherein the electronics channel includes a signal booster positioned along the electronics channel.

* * * * *